United States Patent [19]

Klicker

[11] 4,283,572

[45] Aug. 11, 1981

[54] CONVERSION OF ALKYL PHENYL ETHER TO ALKYLPHENOL

[75] Inventor: James D. Klicker, Morgantown, W. Va.

[73] Assignee: Borg-Warner Corporation, Chicago, Ill.

[21] Appl. No.: 107,690

[22] Filed: Dec. 27, 1979

[51] Int. Cl.[3] .......... C07C 39/06

[52] U.S. Cl. .......... 568/783; 568/780; 568/793

[58] Field of Search .......... 568/783, 780, 793

[56] References Cited

U.S. PATENT DOCUMENTS

| | | | |
|---|---|---|---|
| 2,289,886 | 7/1942 | Schmerling | 568/716 |
| 2,697,732 | 12/1954 | Mavity | 568/805 |
| 3,037,052 | 5/1952 | Bortnick | 260/485 |
| 3,257,467 | 6/1966 | O'Neil et al. | 568/780 |

*Primary Examiner*—Werren B. Lone
*Attorney, Agent, or Firm*—Joseph Shekleton

[57] ABSTRACT

A process for the conversion of an alkyl phenyl ether to the corresponding alkylphenol, involving heating in the presence of a dehydrated sulfonic acid type cation exchange resin having a macroreticular structure. The process has particular application to the recovery of unreacted alkylphenol from a product mixture resulting from a reaction in which the alkylphenol is used (in stoichiometrically excessive amounts) as a reactant.

2 Claims, No Drawings

CONVERSION OF ALKYL PHENYL ETHER TO ALKYLPHENOL

This invention relates as indicated to a process for the conversion of an alkyl phenyl ether to an alkylphenol. More particularly, it relates to a method for recovering a maximum proportion of alkylphenol from a product mixture where the alkylphenol is employed as a reactant and especially where it is thus used in stoichiometrically excessive amounts. Generally, in such instances the unreacted alkylphenol must be recovered after the reaction so that it is available for recycling.

Unfortunately, the alkylphenol, which in turn is prepared by the alkylation of phenol, invariably is contaminated by a small proportion of alkyl phenyl ether. This contaminant usually remains unchanged in reactions of the type contemplated above so that it accumulates along with the unreacted alkylphenol which is recovered. The net result is that the concentration of this alkyl phenyl ether contaminant gradually increases as successive portions of unreacted alkylphenol are recovered and reused, until finally the concentration of alkylphenol is so low that its further reuse is not practical. This presents a disposal problem, an increasingly serious matter in the light of present serious concern about environmental conditions.

U.S. Pat. No. 2,289,886 (Schmerling) shows a process for de-etherizing alkyl phenyl ether by reaction with hydrogen fluoride at a temperature within the range of 50°-200° C. The products of the reaction are phenol and an alkylated phenol.

U.S. Pat. No. 3,257,467 (O'Neil et al) shows the reaction of phenol with a low molecular weight olefin-polymer to produce an alkylated phenol. The reaction is catalyzed by a sulfonated styrene resin cross-linked with about 4% by weight of divinyl benzene.

U.S. Pat. No. 3,037,052 (Bortnick) shows the use of macroreticular sulfonic acid cation exchange resins as catalysts in reactions normally catalyzed by conventional soluble strong acid catalysts. Specifically shown is the use of such a macroreticular resin in the catalysis of the alkylation of phenol.

The invention here is a process for the conversion of an alkyl phenyl ether to the corresponding alkylphenol comprising heating the alkyl phenyl ether in the presence of a dehydrated sulfonic acid type cation exchange resin, at a temperature with the range of from about 60° C. to about 120° C. An especially preferred resin for the above process is one having a macroreticular structure.

The above macroreticular cation exchange resin and its method of preparation are described in U.S. Pat. No. 3,037,052 (Bortnick) referred to earlier herein and the disclosure of that patent is incorporated herein by reference. Briefly, the term "macroreticular" refers to a unique porous structure. This structure is developed, for example, when styrene and divinylbenzene are copolymerized in a solvent which dissolves these monomers, but does not dissolve the resulting polymer. Such solvents are termed "precipitants" in the above Bortnick patent. Typical precipitants include n-butanol, sec-butanol, tert-amyl alcohol, n-hexanol and decanol.

The macroreticular catalyst herein is prepared from a macroreticular polymer as above by sulfonation with concentrated sulfuric acid, oleum, sulfur trioxide or chlorosulfonic acid. The sulfonated resin must then be dehydrated, usually by heating at a temperature of 90°-125° C. at reduced pressure, e.g., 5-10 mm. Azeotropic distillation, e.q., with toluene, heptane, phenol, etc., may also be employed.

The reaction which illustrates the above conversion is shown below

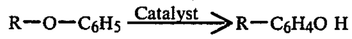

$$R-O-C_6H_5 \xrightarrow{\text{Catalyst}} R-C_6H_4OH$$

operation proceeds and when the concentration reaches about 30% it is advisable to convert the nonyl phenyl ether to nonylphenol. Thus, in the ordinary practice of the conversion process of this invention, the alkyl phenyl ether comprises from about 20% to about 50% of a mixture, the rest of the mixture being principally nonylphenol together with smaller quantities of phenol and dinonylphenol.

Another utilization of the process herein involves passing the alkyl phenyl ether over a fixed bed containing the catalyst. In this way the process can be carried out in a continuous manner. In such cases the concentration of the alkyl phenyl ether will usually be within the range of from about 0.5% to about 10% of the conversion mixture.

The process is illustrated by the following examples.

EXAMPLE 1

A mixture of 43 parts of nonyl phenyl ether, 51 parts of nonylphenol, 4 parts of phenol and 1 part of dinonylphenol is stirred with 15% by weight of a dehydrated sulfonic acid type cation exchange resin having a macroreticular structure, and heated for 2 hours at 80° C. Upon cooling, the mixture is found to contain 0.4 part of nonyl phenyl ether, 66 parts of nonylphenol, 19 parts of phenol and 13 parts of dinonylphenol.

EXAMPLE 2

When the same mixture as in Example 1 is heated with a similar catalyst, except that it does not have a macroreticular structure, at a temperature of 100° C. for 21 hours, the resulting mixture is found to contain 23 parts of nonyl phenyl ether, 55 parts of nonylphenol, 10 parts of phenol and 3 parts of dinonylphenol. where R is alkyl. R may be any alkyl having from about four to about twelve carbon atoms. The process is especially applicable to nonylphenol.

The amount of catalyst which should be employed in the process herein may range from about 0.1% to about 20% based on the weight of the conversion mixture. A preferred range is from about 1% to about 10%.

The temperature of the conversion as indicated, ordinarily will be within the range of from about 60° C. to about 120° C. Where the resin catalyst has a macroreticular structure, as preferred, this temperature range will be from about 60° C. to about 100° C.

The conversion mixture prior to conversion usually will contain a substantial proportion of alkylphenol and lesser amounts of phenol and dialkylphenol. The formation of alkylphenol in the conversion reaction is accompanied by the formation also of some dialkylphenol. This latter reaction can be suppressed to a large extent by adding phenol to the conversion mixture and, in fact, this is a preferred method of carrying out the conversion. This particular advantage is realized by adding to the conversion mixture from about 10% to about 200% of phenol, based on the weight of the conversion mixture. Even then, some dialkylphenol is formed, but in very much reduced amounts. Removal of the excess phenol by stripping is a relatively simple matter.

As indicated earlier, a typical utilization of the conversion process of the invention permits the efficient recovery of unreacted alkylphenol from a product mixture resulting from a reaction in which the alkylphenol is used (in excess) as a reactant. This mixture will contain, in addition to the desired product, a substantial proportion of nonylphenol plus minor amounts of phenol, dinonylphenol and nonyl phenyl ether. These are removed by distillation from the product mixture and recycled back into a fresh reaction mixture. The nonyl phenyl ether accumulates as this recycling

EXAMPLE 3

A mixture somewhat similar to that of Examples 1 and 2, except that it contains a larger amount of phenol, so as to suppress the formation of dinonylphenol, is treated as follows: The mixture contains 24 parts of nonylphenol, 21 parts of nonyl phenyl ether, 55 parts (as compared to 4 parts in the previous examples) of phenol and 1 part of dinonylphenol. It is heated in the presence of 2% by weight of a dehydrated sulfonic acid type cation exchange resin having a macroreticular structure, at a temperature of 60° C. for 3 hours, then at 70° C. for 9 hours. The resulting mixture contains 40 parts of nonylphenol, 2.5 parts of nonyl phenyl ether, 54 parts of phenol and 3 parts of dinonylphenol.

EXAMPLE 4

A vertical glass column, 0.95 inch in diameter and 28 inches high, is filled with a dehydrated sulfonic acid type cation exchange resin (pellets). The column is heated at 100° C. while a mixture of 50 parts of phenol and 50 parts of a nonyl phenyl ether-nonyl-phenol-dinonylphenol-phenol mixture is passed through at a rate of 6–8 ml./min. Samples of the effluent are taken periodically and analyzed. The data obtained from these analyses are shown in the Table.

TABLE

| Sample (vol.) | Ether | Dinonylphenol | Phenol | Nonylphenol |
|---|---|---|---|---|
| feed | 16.1 | 0.6 | 55.1 | 30.3 |
| 228 ml. | 0.9 | 2.6 | 55.4 | 42.0 |
| 234 ml. | 0.9 | 2.5 | 56.6 | 40.7 |
| 232 ml. | 0.9 | 2.3 | 56.4 | 41.1 |
| 230 ml. | 0.9 | 2.4 | 56.0 | 41.3 |
| 126 ml. | 1.4 | 2.1 | 56.7 | 41.0 |

All parts and percentages herein, unless otherwise expressly stated, are by weight.

I claim:

1. A process for the conversion of an alkyl phenyl ether to the corresponding alkylphenol comprising heating an nonyl phenyl ether in the presence of a dehydrated sulfonic acid type cation exchange resin, at a temperature within the range of from about 60° C. to about 120° C.

2. The process of claim 1 wherein the dehydrated sulfonic acid type cationic exchange resin has a macroreticular structure.

* * * * *